United States Patent [19]

Treace

[11] 4,174,716
[45] Nov. 20, 1979

[54] MYRINGOTOMY TUBE

[75] Inventor: Harry T. Treace, Forest Hill, Tenn.

[73] Assignee: Richards Manufacturing Co., Inc., Memphis, Tenn.

[21] Appl. No.: 861,716

[22] Filed: Dec. 19, 1977

[51] Int. Cl.$^2$ .......................................... A61M 27/00
[52] U.S. Cl. ................................................ 128/350 R
[58] Field of Search ............... 128/303 R, 305, 329 R, 128/330, 341, 348, 350 R, 351, DIG. 14

[56] References Cited

U.S. PATENT DOCUMENTS

| | | | |
|---|---|---|---|
| 3,645,268 | 2/1972 | Capote | 128/305 R X |
| 3,871,380 | 3/1975 | Heros | 128/350 R |

FOREIGN PATENT DOCUMENTS 1368758  10/1974  United Kingdom ............... 128/350 R

OTHER PUBLICATIONS

Richards Manufacturing Company Catalog, 1966, Memphis, Tenn., Teflon Armstrong Beveled Drain Tube, (Grommet Type) No. 2106.

*Primary Examiner*—Henry J. Recla

*Attorney, Agent, or Firm*—John R. Walker, III

[57] ABSTRACT

A myringotomy tube device which obviates the inimical natural tendency of the healing incision to cause spontaneous extrusion of the device. The device is characterized by an inner flange member having a shape substantially resembling a top view of a canoe which establishes sharp tapered portions to individually facilitate initial engagement of the device with a lip portion of the tympanic membrane defining a surgical incision applied thereto. Included is a principal or tubular member which extends through the incision provided in the tympanic membrane for communicating the middle ear with the external auditory canal. The tubular member is conspicuously pinched in adjacent the middle of the length thereof to establish a minimal diameter portion upon which the lip portion of the incision is urged to ride, i.e., being urged thereon by the inwardly sloping annular surface. Also, the external surface of the tubular member is elliptically shaped in cross section which conforms the lip of the healing incision toward an unnatural elliptical shape which is contributory in precluding spontaneous extrusion of the device.

14 Claims, 5 Drawing Figures

U.S. Patent  Nov. 20, 1979  4,174,716
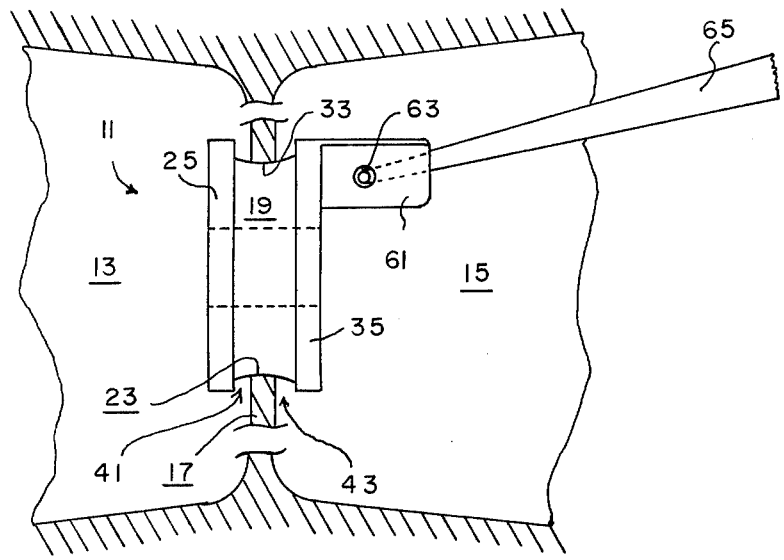
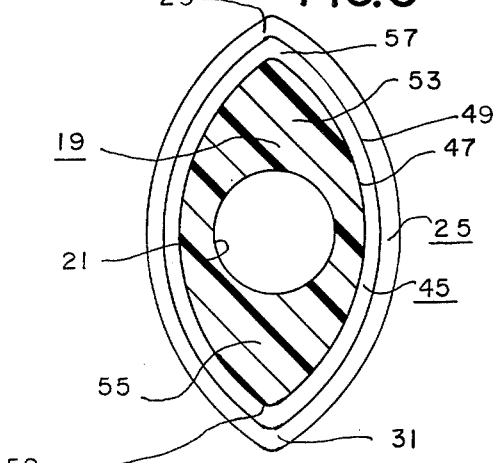
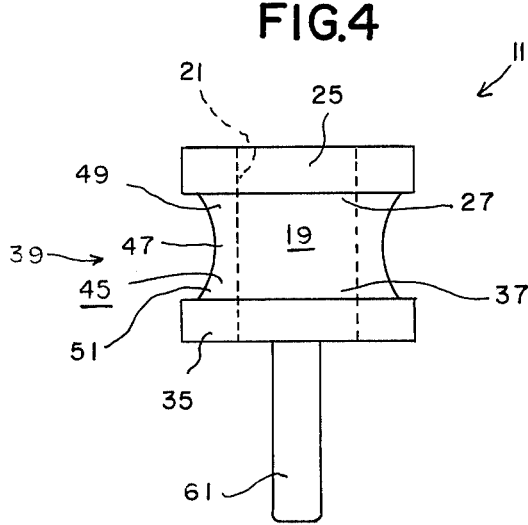
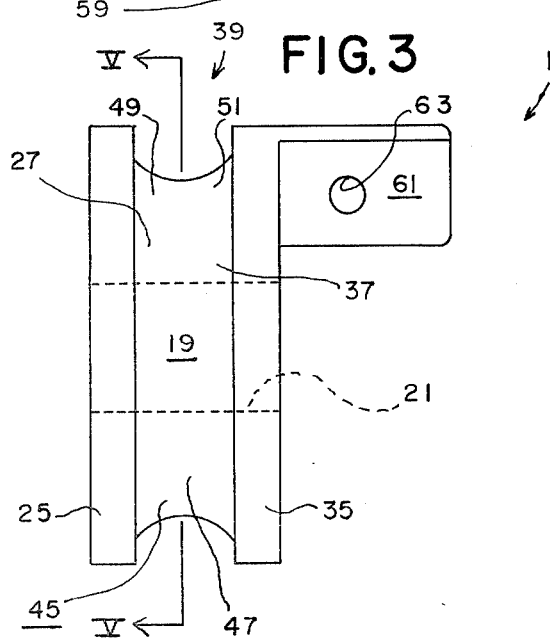
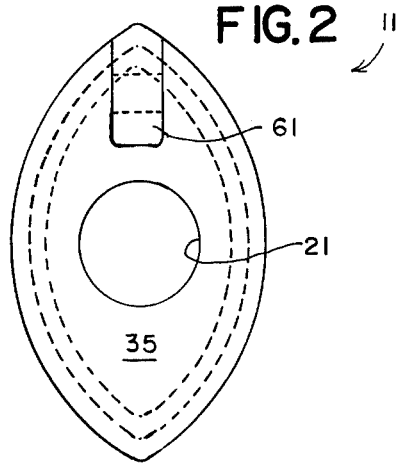

MYRINGOTOMY TUBE

BACKGROUND OF THE INVENTION

1. Field of the Invention

This invention relates to the field of otology instruments and implants and is particularly directed toward a myringotomy tube.

2. Description of the Prior Art

Numerous different configured myringogomy tubes have heretofore been patented. See, for example, the U.S. Pat. No. 3,807,409 to Paparella, and particularly the "other publications" listed under the heading "References Cited" thereof. Additionally, a U.S. Pat. No. 3,871,380 to Heros and U.S. Pat. No. Des. 239,330 to Shea disclose myringotomy tubes for the same general purpose as herein disclosed. However, none of the above mentioned patents suggest or disclose applicant's device.

Several problems prevail in the state of the art with myringotomy tubes. A few of these problems are: first, the internal fluid pressure often extrudes the device or prosthesis outwardly into the auditory canal. This problem is well known to those skilled in the art and it is called spontaneous extrusion of the prosthesis and this inimical situation usually occurs prematurely which of course presents further complications.

A second well known problem involves the initial insertion of the prosthesis into the tympanic membrane. As pointed out in the Paparella U.S. Pat. No. 3,807,409, this is complicated by the fact that the ear canal is a small, tortuous path which makes it difficult to both see and manipulate instruments in the confined space. In order to overcome these problems, a relatively large wound opening into the tympanic membrane is first incised, and then the prosthesis placed therein. Since the wound opening is usually oversize, the spontaneous extrusion of the prosthesis is simpler than it would otherwise be.

A third problem involves the difficulty experienced in removing the prosthesis from the tympanic membrane in those cases where the condition has been cured prior to the spontaneous extrusion of the prosthesis. The removal is normally accomplished by grasping the outer flange of the prosthesis with small forceps which are pulled outwardly. Unfortunately, this procedure often results in injury to the tympanic membrane while attempting to accomplish removal.

SUMMARY OF THE INVENTION

The present invention is directed towards overcoming the problems and disadvantages relative to prior myringotomy tubes. Indeed, the present invention is intended to alleviate the several problems above enumerated. The device is characterized by an inner flange member having a shape substantially resembling a top view of a canoe which establishes sharp tapered portions to individually facilitate initial engagement of the device with a lip portion of the tympanic membrane defining a surgical incision applied thereto. Included is a principal or tubular member which extends through the incision provided in the tympanic membrane for communicating the middle ear with the external auditory canal. The tubular member is pinched in annularly adjacent the middle of the length thereof to establish a minimal diameter portion upon which the lip portion of the incision is urged to ride, i.e., being urged thereon by the inwardly sloping annular surface. Also, the external surface of the tubular member is elliptical shape in cross section which conforms the lip of the healing incision toward an unnatural elliptical shape which is contributory in precluding either spontaneous extrusion or migratory intrusion of the device. Additionally, the device includes a tab member provided with an aperture for readily accommodating the working end of a right angle pick instrument which may be received therein during insertion and/or removal of the device.

DESCRIPTION OF THE DRAWING

FIG. 1 is a side elevational view of the myringotomy tube of the present invention shown in use in a patient's ear with a right angle pick instrument being depicted in a preferred manner for inserting and/or removing the prosthesis therefrom.

FIG. 2 is a front elevational view of the device of the present invention.

FIG. 3 is a side elevational view substantially like FIG. 1 with the view being taken from the left side of FIG. 2.

FIG. 4 is a top plan view taken as looking down on FIG. 2.

FIG. 5 is a sectional view taken as on the line V—V of FIG. 3.

DESCRIPTION OF THE PREFERRED EMBODIMENT

From FIG. 1 of the drawings it may clearly be seen that the myringotomy tube or device 11 of the present invention is intended for providing ventilation and drainage of the middle ear, indicated at 13, through the external auditory canal, indicated at 15, of a patient. The device 11 is shown properly inserted or attached to the tympanic membrane, indicated at 17, of the patient in a manner to be fully disclosed as the specification proceeds. In general terminology, the myringotomy tube 11 includes a principal member 19 having a passageway, as at 21 in FIGS. 2 and 5, provided therein for communicating the middle ear 13 with the external auditory canal 15 subsequent to the principal member 19 having been inserted through a surgical incision, indicated at 23, having been applied to the tympanic membrane 17. Of course, it should be appreciated that the overall size of the device 11 as measured along the major axis thereof (FIG. 5) preferably is a nominal 3⅓ mm while the overall dimension along the minor axis thereof is preferably a nominal 2 mm. However, it should be understood that the size of the device 11 may vary considerably since the above mentioned dimensions are for illustration purposes only so as to convey a more meaningful understanding of the specification to follow.

In order to overcome certain problems relative to prior myringotomy tubes and as mentioned in the Paparella patent, a relatively large wound opening into the tympanic membrane is first incised, and then the myringotomy tube is placed therein. Since the wound opening is usually oversize, i.e., for certain of these prior devices, the spontaneous extrusion of the device is simpler than it would otherwise be, e.g., the size of the wound opening preferably should be substantially no larger than the cross section or diameter of the main tube portion or principal member 19. Obviously, this is not always easily accomplished for various reasons: first, the very nature of microsurgery makes it most difficult to insert many of the prior devices. Secondly, certain of these prior devices did not include any structure for facilitating inserting the device through a tightly fitting incision, thus necessitating the wound opening to be oversize.

The device 11 also includes an inner flange member 25 integrally combined with the principal member 19 and which is disposed at the innermost end of the principal member 19, as at 27, for precluding at least in part the inimical natural tendency of the healing incision 23 to cause the device 11 to be spontaneously extruded into the external auditory canal 15. The inner flange member 23 includes at least one but preferably a pair of sharply tapered portions 29, 31 integrally combined with the inner flange member 25. Either of the tapered portions 29, 31 facilitates initial engagement of the inner flange member 25 with a lip portion, as at 33, of the tympanic membrane 17, i.e., the lip portion 33 defines the incision 23 provided in the membrane 17. Therefore, the tapered portions 29, 31 establish optimum ease in inserting the myringotomy tube 11 through the incision 23, i.e., the incision 23 may now be so small that either of the sharply tapered portions 29, or 31 may facilitate stretching the lip portion 33, if necessary, to assure an initial tight fit of the principal member 19.

The device 11 also includes an outer flange member 35 integrally combined with the principal member 19 and which is disposed at the outermost end, as at 37, of the principal member 19 for precluding, at least in part, the inimical migratory intrusion of the myringotomy tube 11 into the middle ear 13.

The device 11 includes means, e.g., annular gradient means generally indicated at 39, for causing the principal member 19 to be urged a predetermined distance inwardly of the middle ear 13. The gradient means 39 causes the inner flange member 25 to be situated a spaced distance, as at 41, inwardly from the tympanic membrane 17 during the healing process of the incision 23. Thus, spontaneous extrusion of the device 11 is substantially obviated. In other words, the principal member 19 preferably is pinched in gradiently so as to inherently be urged toward a substantially equilibrium condition, i.e., as clearly indicated in FIG. 1 of the drawings. Moreover, neither the inner nor the outer flange member 25, 37 engages the tympanic membrane 17 during the healing process of the incision 23. Accordingly, the inimical spontaneous extrusion and migratory intrusion of the myringotomy tube 13, of course, are both substantially obviated. Thus, it may be seen that a spaced distance, as at 43, which is substantially equal to the previously mentioned spaced distance 41 is inherently caused to be maintained during the lengthy healing process, i.e., the healing process may continue for several months.

At this point it might be beneficial to digress momentarily and discuss certain physical properties or characteristics pertaining to the middle ear 13 and the tympanic membrane 17. A well known fact is that the internal fluid pressure of the middle ear often extrudes the myringotomy tube outwardly into the external auditory canal 15. Often this occurs prior to sufficient time for the curing or alleviation of the condition which initially required the insertion of the myringotomy tube. Additionally, the healing process of the wound opening involves the natural accumulation or formation of ever decreasing concentric circles of tissue which eventually effect closure of the incision 23. Therefore, inherently, the healing process is constantly applying an annular squeezing force about the myringotomy tube which, of course, heretofore contributed toward the delayed spontaneous extrusion of these prior myringotomy tubes, i.e., evidenced by the fact that spontaneous extrusion often occurred several months after the initial insertion of the device.

Therefore, the annular gradient means 39 alluded to above aids significantly in precluding the inimical spontaneous extrusion and migratory intrusion of the myringotomy tube 11. The annular gradient means 39 includes means, e.g., a nonuniform thickness tubular wall 45 defining the principal member 19, for (1) establishing a minimal outer diameter portion, as at 47, of the principal member 19 with the minimal outer diameter portion 47 being disposed adjacent the middle of the length of the principal member 19 and for (2) establishing greater outer diameter portions, as at 49, 51, disposed respectively adjacent the inner and outer flange members 25, 35, viz., the outer diameter of the principal member 19 gradually increases radially outwardly from the minimal diameter portion 47 toward either end 27, 37 thereof or toward the inner and outer flange members 25, 35.

In addition to being constructed so as to establish the minimal outer diameter portion 47 and the greater diameter portion 49, 51 (or being radially pinched in) the external surface of the principal member 19 preferably is elliptically shaped in cross section. This unusual elliptical shape continuously conforms the lip portion 33 of the tympanic membrane 17 (defining the incision 23 provided therein) toward an unnatural elliptical shape as the healing process develops, i.e., utilizing to an inherent advantage the tendency of the incision to heal in concentric circles, as mentioned above. Therefore, the elliptical shape of the principal member 19 further aids in precluding spontaneous extrusion of the myringotomy tube.

More specifically, the passageway 21 is circular in cross section as clearly shown in FIG. 5 and is defined by the previously mentioned non-uniform thickness tubular wall 45 or annular gradient means 39. However, the wall 45 also includes a pair of remotely disposed thick portions, as at 53, 55 in FIG. 5 of the drawing, thus establishing the elliptical shape, viz., the portions 53, 55 are sharply tapered in cross section at the exterior surfaces thereof, as at 57, 59, respectively. Incidentally, the tapered portions 57, 59 preferably are aligned with and correspond respectively to the sharply tapered portions 29, 31 of the inner flange member 25.

In other words the non-uniform thickness of the tubular wall 45 is so constructed that the external surface thereof is not only elliptical shaped at 53, 55 but it also expands gradually annularly from the previously mentioned minimal portion 47. Therefore, it may alternately be stated that the minimal portion 47 is disposed a spaced distance from the inner flange member 25 and the wall 45 not only is elliptical shaped in cross section but it, also, expands gradiently toward the previously mentioned greater outer diameter portions (or maximum portions 49, 51) for causing the myringotomy tube 11 to inherently tend to be urged toward the minimal portion 47 (or to assume an optimum equilibrium condition) as the healing process of the wound opening (or incision 23) develops.

The device 11 also includes tab means, as at 61, which is integrally combined with the outer flange member 35 for facilitating insertion and removal of the device 11. More specifically, the tab means 61 is provided with an aperture, as at 63, for accommodating the working end of a right angle pick instrument, indicated at 65 in FIG. 1, which may be received within the aperture 63 during insertion and/or removal of the device 11.

Although the invention has been described and illustrated with respect to a preferred embodiment thereof, it should be understood that it is not to be so limited since changes and modifications may be made therein which are within the full intended scope of the invention.

I claim:

1. A myringotomy tube for providing ventilation and drainage of the middle ear through the external auditory canal, said myringotomy tube comprising a principal member having a passageway provided therein for communicating the middle ear with the external auditory canal subsequent to said principal member having been inserted through a surgical incision applied to the tympanic membrane, an inner flange member integrally combined with said principal member and being disposed at the innermost end thereof for precluding at least in part the inimical natural tendency of the healing incision to cause said myringotomy tube to be spontaneously extruded into the external auditory canal, and the external surface of said inner flange member being substantially elliptical shaped in cross-section as taken on a plane normal to said passageway for facilitating initial engagement thereof with a lip portion of the tympanic membrane defining the incision provided therein to establish optimum ease in the insertion of said myringotomy tube through the incision.

2. The myringotomy tube as set forth in claim 1 in which is included means for causing said principal member to be urged a predetermined distance inwardly of the middle ear with said inner flange member being situated a spaced distance inwardly from the tympanic membrane during the healing process of the incision whereby spontaneous extrusion of the myringotomy tube is substantially obviated.

3. A myringotomy tube for providing ventilation and drainage of the middle ear through the external auditory canal, said myringotomy tube comprising a principal member having a passageway provided therein for communicating the middle ear with the external auditory canal subsequent to said principal member having been inserted through a surgical incision applied to the tympanic membrane, a inner flange member integrally combined with said principal member and being disposed at the innermost end thereof for precluding at least in part the inimical natural tendency of the healing incision to cause said myringotomy tube to be spontaneously extruded into the external auditory canal, and said inner flange member including at least one sharply tapered portion integrally combined therewith for facilitating initial engagement thereof with a lip portion of the tympanic membrane defining the incision provided therein to established optimum ease in the insertion of said myringotomy tube through the incision, the external surface of said principal member being elliptical shaped in cross-section for engaging and conforming the lip portion of the tympanic membrane defining the incision provided therein toward an unnatural elliptical shape as the healing process develops to further aid in precluding spontaneous extrusion of the myringotomy tube.

4. The myringotomy tube as set forth in claim 3 in which is included means for causing said principal member to be urged a predetermined distance inwardly of the middle ear with said inner flange member being situated a spaced distance inwardly from the tympanic membrane during the healing process of the incision whereby spontaneous extrusion of the myringotomy tube is substantially obviated.

5. A myringotomy tube for providing ventilation and drainage of the middle ear through the external auditory canal, said myringotomy tube comprising a principal member having a passageway provided therein for communicating the middle ear with the external auditory canal subsequent to said principal member having been inserted through a surgical incision applied to the tympanic membrane, an inner flange member integrally combined with said principal member and being disposed at the innermost end thereof for precluding at least in part the inimical natural tendency of the healing incision to cause said myringotomy tube to be spontaneously extruded into the external auditory canal, the external surface of said inner flange member being substantially elliptical shaped in cross-section as taken on a plane normal to said passageway for facilitating initial engagement thereof with a lip portion of the tympanic membrane defining the incision provided therein to extablish optimum ease in the insertion of said myringotomy tube through the incision, and an outer flange member integrally combined with said principal member and being disposed at the outermost end thereof for precluding at least in part the inimical migratory intrusion of said myringotomy tube into the middle ear.

6. The myringotomy tube as set forth in claim 5 in which is included means for causing said principal member to be urged toward a substantially equilibrium condition wherein neither of said inner and outer flange members engages the tympanic membrane during the healing process of the incision whereby the inimical spontaneous extrusion and migratory intrusion of said myringotomy tube are substantially obviated.

7. A myringotomy tube for providing ventilation and drainage of the middle ear through the external auditory canal, said myringotomy tube comprising a principal member having a passageway provided therein for communicating the middle ear with the external auditory canal subsequent to said principal member having been inserted through a surgical incision applied to the tympanic membrane, an inner flange member integrally combined with said principal member and being disposed at the innermost end thereof for precluding at least in part the inimical natural tendency of the healing incision to cause said myringotomy tube to be spontaneously extruded into the external auditory canal, said inner flange member including a pair of remotely disposed sharply tapered portions integrally combined therewith for individually facilitating initial engagement thereof with a lip portion of the tympanic membrane defining the incision provided therein to establish optimum ease in the insertion of said myringotomy tube through the incision, and an outer flange member integrally combined with said principal member and being disposed at the outermost end thereof for precluding at least in part the inimical migratory intrusion of said myringotomy tube into the middle ear, the external surface of said principal member being elliptical shaped in cross-section for engaging and conforming that portion of the tympanic membrane defining the incision provided therein toward an unnatural elliptical shape as the healing process develops to further aid in precluding spontaneous extrusion of the myringotomy tube.

8. The myringotomy tube as set forth in claim 7 in which said elliptical shaped external surface expands gradually annularly from a minimal portion disposed a spaced distance from said inner flange member toward a maximum portion disposed adjacent said inner flange member for causing said myringotomy tube to tend to be urged toward said minimal portion as the healing process of the incision develops.

9. The myringotomy tube as set forth in claim 7 in which said principal member includes annular gradient means for further aiding in precluding the inimical spontaneous extrusion and migratory intrusion of the myringotomy tube, said annular gradient means includes means for (1) establishing a minimal outer diameter portion of said principal member with said minimal outer diameter portion being disposed adjacent the middle of the length thereof and (2) for establishing greater outer diameter portions disposed respectively adjacent said inner and outer flange members with the outer diameter of said principal member gradually increasing radially outwardly from said minimal outer diameter portion toward either end thereof.

10. A myringotomy tube providing ventilation and drainage of the middle ear through the external auditory canal, said myringotomy tube comprising a principal member having a passageway provided therein for communicating the middle ear with the external auditory canal subsequent to said principal member having been inserted through a surgical incision applied to the tympanic membrane, an inner flange member integrally combined with said principal member and being disposed at the innermost end thereof for precluding at least in part the inimical natural tendency of the healing incision to cause said myringotomy tube to be spontaneously extruded into the external auditory canal, said inner flange member including a pair of remotely disposed sharply tapered portions integrally combined therewith for individually facilitating initial engagement thereof with a lip portion of the tympanic membrane defining the incision provided therein to establish optimum ease in the insertion of said myringotomy tube through the incision, and an outer flange member integrally combined with said principal member and being disposed at the outermost end thereof for precluding at least in part the inimical migratory intrusion of said myringotomy tube into the middle ear, said passageway being circular in cross-section and being defined by a wall having an irregular thickness, said wall including a pair of remotely disposed thick portions which are sharply tapered in cross-section at the exterior surfaces thereof for engaging and comforming that portion of the tympanic membrane defining the incision provided therein toward an unnatural elliptical shape as the healing process develops to further aid in precluding spontaneous extrusion of the myringotomy tube.

11. The myringotomy tube as set forth in claim 5 in which is included tab means integrally combined with said outer flange member for facilitating insertion and removal of said myringotomy tube.

12. The myringotomy tube as set forth in claim 5 in which said tab means is provided with an aperture extending therethrough at a right angle for accommodating the working end of a right angle pick instrument which may be received during insertion and/or removal of said myringotomy tube.

13. The myringotomy tube as set forth in claim 5 in which said principal member includes annular gradient means for further aiding in precluding the inimical spontaneous extrusion and migratory intrusion of said myringotomy tube, said annular gradient means includes means for (1) establishing a minimal outer diameter portion of said principal member with said minimal outer diameter portion being disposed adjacent the middle of the length thereof and (2) for establishing greater outer diameter portions disposed respectively adjacent said inner and outer flange members with the outer diameter of said principal member gradually increasing radially outwardly from said minimal outer diameter portion toward either end thereof.

14. A myringotomy tube (for providing ventilation and drainage of the middle ear through the external auditory canal,) said myringotomy tube comprising a principal member having a passageway provided therein (for communicating the middle ear with the external auditory canal subsequent to said principal member having been inserted through a surgical incision applied to the tympanic membrane,) an inner flange member combined with said principal member (for precluding at least in part the natural tendency of the healing incision to cause said myringotomy tube to be spontaneously extruded into the external auditory canal), the external surface of said principle member being substantially elliptical shaped in cross-section.

* * * * *